United States Patent
Wixey

(10) Patent No.: US 11,517,312 B2
(45) Date of Patent: Dec. 6, 2022

(54) SURGICAL INSTRUMENT WITH LOCKOUT MECHANISM

(71) Applicant: INTUITIVE SURGICAL OPERATIONS, INC., Sunnyvale, CA (US)

(72) Inventor: Matthew Wixey, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 39 days.

(21) Appl. No.: 16/966,099

(22) PCT Filed: Feb. 12, 2019

(86) PCT No.: PCT/US2019/017646
§ 371 (c)(1),
(2) Date: Jul. 30, 2020

(87) PCT Pub. No.: WO2019/157500
PCT Pub. Date: Aug. 15, 2019

(65) Prior Publication Data
US 2021/0022736 A1 Jan. 28, 2021

Related U.S. Application Data

(60) Provisional application No. 62/629,572, filed on Feb. 12, 2018.

(51) Int. Cl.
*A61B 17/072* (2006.01)
*A61B 17/28* (2006.01)

(52) U.S. Cl.
CPC .... *A61B 17/07207* (2013.01); *A61B 17/2841* (2013.01); *A61B 2017/07271* (2013.01);
(Continued)

(58) Field of Classification Search
CPC .......... A61B 17/07207; A61B 17/2841; A61B 2017/07271; A61B 2017/07278; A61B 2017/07285; A61B 2017/2845
(Continued)

(56) References Cited

U.S. PATENT DOCUMENTS 4,305,539 A 12/1981 Korolkov et al.
4,319,576 A 3/1982 Rothfuss
(Continued)

FOREIGN PATENT DOCUMENTS

EP 0277532 B1 8/1990
EP 0277529 B1 4/1993
(Continued)

OTHER PUBLICATIONS

International Search Report and Written Opinion for Application No. PCT/US2020/054568, dated Jan. 29, 2021, 13 pages.
(Continued)

*Primary Examiner* — Stephen F. Gerrity
*Assistant Examiner* — Linda J Hodge
(74) *Attorney, Agent, or Firm* — Farber LLC

(57) ABSTRACT

Locking assemblies for surgical clamping and cutting instruments include a locking member and a switch. A drive member may be configured to releasably engage a knife and/or a shuttle of the surgical instrument for translating the knife and/or shuttle in a distal direction through a firing stroke. The locking member is movable from a first position permitting distal translation of the drive member through the firing stroke, and a second position inhibiting distal translation of the drive member through the firing stroke. A switch, when proximally positioned, releasably engages the locking member to maintain the locking member in the first position. The switch disengages from the locking member when the switch is moved to a distal position.

10 Claims, 13 Drawing Sheets

(52) U.S. Cl.
CPC .............. *A61B 2017/07278* (2013.01); *A61B 2017/07285* (2013.01); *A61B 2017/2845* (2013.01)

(58) Field of Classification Search
USPC .......................................... 227/175.2–175.4
See application file for complete search history.

(56) References Cited

U.S. PATENT DOCUMENTS

| | | |
|---|---|---|
| 4,429,695 A | 2/1984 | Green |
| 4,509,518 A | 4/1985 | McGarry et al. |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,767,044 A | 8/1988 | Green |
| 4,809,695 A | 3/1989 | Gwathmey et al. |
| 4,848,637 A | 7/1989 | Pruitt |
| 4,892,244 A | 1/1990 | Fox et al. |
| 4,930,503 A | 6/1990 | Pruitt |
| 4,978,049 A | 12/1990 | Green |
| 5,027,834 A | 7/1991 | Pruitt |
| 5,040,715 A | 8/1991 | Green et al. |
| 5,133,735 A | 7/1992 | Slater et al. |
| 5,133,736 A | 7/1992 | Bales, Jr. et al. |
| 5,180,092 A | 1/1993 | Crainich |
| 5,275,323 A | 1/1994 | Schulze et al. |
| 5,307,976 A | 5/1994 | Olson et al. |
| 5,312,023 A | 5/1994 | Green et al. |
| 5,334,183 A | 8/1994 | Wuchinich |
| 5,342,396 A | 8/1994 | Cook |
| 5,366,133 A | 11/1994 | Geiste |
| 5,452,836 A | 9/1995 | Huitema et al. |
| 5,452,837 A | 9/1995 | Williamson, IV et al. |
| 5,480,089 A | 1/1996 | Blewett |
| 5,484,095 A | 1/1996 | Green et al. |
| 5,484,451 A | 1/1996 | Akopov et al. |
| 5,487,500 A | 1/1996 | Knodel et al. |
| 5,497,931 A | 3/1996 | Nakamura |
| 5,533,521 A | 7/1996 | Granger |
| 5,540,375 A | 7/1996 | Bolanos et al. |
| 5,554,164 A | 9/1996 | Wilson et al. |
| 5,560,530 A | 10/1996 | Bolanos et al. |
| 5,562,239 A | 10/1996 | Boiarski et al. |
| 5,571,116 A | 11/1996 | Bolanos et al. |
| 5,571,285 A | 11/1996 | Chow et al. |
| 5,615,820 A | 4/1997 | Viola |
| 5,624,452 A | 4/1997 | Yates |
| 5,628,446 A | 5/1997 | Geiste et al. |
| 5,667,626 A | 9/1997 | Cayford et al. |
| 5,676,674 A | 10/1997 | Bolanos et al. |
| 5,688,269 A | 11/1997 | Newton et al. |
| 5,690,269 A | 11/1997 | Bolanos et al. |
| 5,693,042 A | 12/1997 | Boiarski et al. |
| 5,697,542 A | 12/1997 | Knodel et al. |
| 5,709,680 A | 1/1998 | Yates et al. |
| 5,752,644 A | 5/1998 | Bolanos et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,792,135 A | 8/1998 | Madhani et al. |
| 5,820,009 A | 10/1998 | Melling et al. |
| 5,826,776 A | 10/1998 | Schulze et al. |
| 5,833,695 A | 11/1998 | Yoon |
| 5,865,361 A | 2/1999 | Milliman et al. |
| 5,871,135 A | 2/1999 | Williamson, IV et al. |
| 5,911,353 A | 6/1999 | Bolanos et al. |
| 5,915,616 A | 6/1999 | Viola et al. |
| 5,941,442 A | 8/1999 | Geiste et al. |
| 5,954,259 A | 9/1999 | Viola et al. |
| 5,959,892 A | 9/1999 | Lin et al. |
| 6,032,849 A | 3/2000 | Mastri et al. |
| 6,079,606 A | 6/2000 | Milliman et al. |
| 6,174,309 B1 | 1/2001 | Wrublewski et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,330,956 B1 | 12/2001 | Willinger |
| 6,330,965 B1 | 12/2001 | Milliman et al. |
| 6,488,196 B1 | 12/2002 | Fenton, Jr. |
| 6,503,259 B2 | 1/2003 | Huxel et al. |
| 6,585,735 B2 | 7/2003 | Frazier et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,786,382 B1 | 9/2004 | Hoffman |
| 6,817,974 B2 | 11/2004 | Cooper et al. |
| 6,877,647 B2 | 4/2005 | Green et al. |
| 6,905,057 B2 | 6/2005 | Swayze et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,114,642 B2 | 10/2006 | Whitman |
| 7,128,253 B2 | 10/2006 | Mastri et al. |
| 7,140,527 B2 | 11/2006 | Ehrenfels et al. |
| 7,140,528 B2 | 11/2006 | Shelton, IV et al. |
| 7,308,998 B2 | 12/2007 | Mastri et al. |
| 7,328,828 B2 | 2/2008 | Ortiz et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,401,721 B2 | 7/2008 | Holsten et al. |
| 7,407,075 B2 | 8/2008 | Holsten et al. |
| 7,455,676 B2 | 11/2008 | Holsten et al. |
| 7,472,814 B2 | 1/2009 | Mastri et al. |
| 7,481,349 B2 | 1/2009 | Holsten et al. |
| 7,494,039 B2 | 2/2009 | Racenet et al. |
| 7,565,993 B2 | 7/2009 | Milliman et al. |
| 7,588,174 B2 | 9/2009 | Holsten et al. |
| 7,673,783 B2 | 3/2010 | Morgan et al. |
| 7,699,835 B2 | 4/2010 | Lee et al. |
| 7,721,930 B2 | 5/2010 | McKenna et al. |
| 7,726,539 B2 | 6/2010 | Holsten et al. |
| 7,770,774 B2 | 8/2010 | Mastri et al. |
| 7,832,611 B2 | 11/2010 | Boyden et al. |
| 7,837,079 B2 | 11/2010 | Holsten et al. |
| 7,866,526 B2 | 1/2011 | Green et al. |
| 7,942,303 B2 | 5/2011 | Shah et al. |
| 7,950,561 B2 | 5/2011 | Aranyi |
| 8,070,035 B2 | 12/2011 | Holsten et al. |
| 8,083,118 B2 | 12/2011 | Milliman et al. |
| 8,127,975 B2 | 3/2012 | Olson et al. |
| 8,157,152 B2 | 4/2012 | Holsten et al. |
| 8,272,553 B2 | 9/2012 | Mastri et al. |
| 8,308,042 B2 | 11/2012 | Aranyi |
| 8,348,127 B2 | 1/2013 | Marczyk |
| 8,365,972 B2 | 2/2013 | Aranyi et al. |
| 8,371,492 B2 | 2/2013 | Aranyi et al. |
| 8,551,091 B2 | 10/2013 | Couture et al. |
| 8,573,465 B2 | 11/2013 | Shelton |
| 8,579,178 B2 | 11/2013 | Holsten et al. |
| 8,608,047 B2 | 12/2013 | Holsten et al. |
| 8,672,939 B2 | 3/2014 | Garrison |
| 8,783,541 B2 | 7/2014 | Shelton, IV et al. |
| 8,800,841 B2 | 8/2014 | Ellerhorst et al. |
| 8,858,547 B2 | 10/2014 | Brogna |
| 8,905,287 B2 | 12/2014 | Racenet et al. |
| 8,925,785 B2 | 1/2015 | Holsten et al. |
| 9,010,606 B2 | 4/2015 | Aranyi et al. |
| 9,192,378 B2 | 11/2015 | Aranyi et al. |
| 9,192,379 B2 | 11/2015 | Aranyi et al. |
| 9,216,019 B2 | 12/2015 | Schmid et al. |
| 9,345,479 B2 | 5/2016 | Racenet et al. |

(56) References Cited

U.S. PATENT DOCUMENTS

| | | |
|---|---|---|
| 9,717,497 B2 | 8/2017 | Zerkle et al. |
| 9,717,498 B2 | 8/2017 | Aranyi et al. |
| 9,936,949 B2 | 4/2018 | Measamer et al. |
| 10,111,659 B2 | 10/2018 | Racenet et al. |
| 10,231,732 B1 | 3/2019 | Racenet et al. |
| 10,285,693 B2 | 5/2019 | Kimsey et al. |
| 10,646,219 B2 | 5/2020 | Racenet et al. |
| 10,828,027 B2 | 11/2020 | Racenet et al. |
| 10,863,988 B2 | 12/2020 | Patel et al. |
| 2002/0165562 A1 | 11/2002 | Grant |
| 2003/0181910 A1 | 9/2003 | Dycus et al. |
| 2004/0232199 A1 | 11/2004 | Shelton et al. |
| 2004/0267310 A1 | 12/2004 | Racenet et al. |
| 2005/0006430 A1 | 1/2005 | Wales |
| 2005/0006434 A1 | 1/2005 | Wales et al. |
| 2005/0070925 A1 | 3/2005 | Shelton, IV et al. |
| 2005/0070958 A1 | 3/2005 | Swayze et al. |
| 2005/0173490 A1 | 8/2005 | Shelton, IV |
| 2005/0178813 A1 | 8/2005 | Swayze et al. |
| 2005/0187576 A1 | 8/2005 | Whitman et al. |
| 2006/0000868 A1 | 1/2006 | Shelton, IV et al. |
| 2006/0016853 A1 | 1/2006 | Racenet |
| 2006/0022014 A1 | 2/2006 | Shelton, IV et al. |
| 2006/0022015 A1 | 2/2006 | Shelton, IV et al. |
| 2006/0024817 A1 | 2/2006 | Deguchi et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0025816 A1 | 2/2006 | Shelton, IV |
| 2006/0049230 A1 | 3/2006 | Shelton, IV et al. |
| 2006/0097026 A1 | 5/2006 | Shelton, IV |
| 2006/0161190 A1 | 7/2006 | Gadberry et al. |
| 2006/0190031 A1 | 8/2006 | Wales et al. |
| 2006/0226196 A1 | 10/2006 | Hueil et al. |
| 2007/0010838 A1 | 1/2007 | Shelton, IV et al. |
| 2007/0045379 A1 | 3/2007 | Shelton, IV |
| 2007/0102475 A1* | 5/2007 | Ortiz ............... A61B 17/07207 227/175.2 |
| 2007/0262116 A1 | 11/2007 | Hueil et al. |
| 2008/0023522 A1 | 1/2008 | Olson et al. |
| 2008/0078804 A1 | 4/2008 | Shelton et al. |
| 2009/0277947 A1 | 11/2009 | Viola |
| 2010/0108740 A1 | 5/2010 | Pastorelli et al. |
| 2010/0145334 A1 | 6/2010 | Olson et al. |
| 2010/0179545 A1 | 7/2010 | Twomey et al. |
| 2011/0022078 A1 | 1/2011 | Hinman |
| 2011/0174863 A1 | 7/2011 | Shelton, IV et al. |
| 2011/0251612 A1 | 10/2011 | Faller et al. |
| 2011/0251613 A1 | 10/2011 | Guerra et al. |
| 2011/0290854 A1 | 12/2011 | Timm et al. |
| 2011/0295270 A1 | 12/2011 | Giordano et al. |
| 2012/0022584 A1 | 1/2012 | Donnigan et al. |
| 2012/0223121 A1 | 9/2012 | Viola et al. |
| 2013/0015231 A1 | 1/2013 | Kostrzewski |
| 2013/0056521 A1 | 3/2013 | Swensgard |
| 2013/0068821 A1 | 3/2013 | Huitema et al. |
| 2013/0087599 A1 | 4/2013 | Krumanaker et al. |
| 2013/0098965 A1* | 4/2013 | Kostrzewski ......... A61B 90/08 227/175.2 |
| 2013/0148577 A1 | 6/2013 | Terry et al. |
| 2013/0248577 A1 | 9/2013 | Leimbach et al. |
| 2013/0296922 A1 | 11/2013 | Allen, IV et al. |
| 2014/0001236 A1 | 1/2014 | Shelton, IV et al. |
| 2014/0025071 A1 | 1/2014 | Sims et al. |
| 2014/0175152 A1 | 6/2014 | Hess et al. |
| 2014/0180286 A1 | 6/2014 | Marczyk et al. |
| 2014/0263546 A1 | 9/2014 | Aranyi |
| 2014/0263550 A1* | 9/2014 | Aranyi ............ A61B 17/07207 227/175.3 |
| 2014/0263559 A1 | 9/2014 | Williams et al. |
| 2014/0263567 A1 | 9/2014 | Williams et al. |
| 2014/0263569 A1* | 9/2014 | Williams ............ A61B 17/068 227/180.1 |
| 2014/0343550 A1 | 11/2014 | Faller et al. |
| 2015/0209037 A1 | 7/2015 | Kostrzewski et al. |
| 2015/0250530 A1 | 9/2015 | Manzo et al. |
| 2015/0272576 A1 | 10/2015 | Cappola |
| 2015/0297227 A1 | 10/2015 | Huitema et al. |
| 2016/0038227 A1 | 2/2016 | Garrison |
| 2016/0120544 A1 | 5/2016 | Shelton, IV et al. |
| 2016/0175033 A1 | 6/2016 | Le |
| 2016/0192999 A1 | 7/2016 | Stulen et al. |
| 2016/0270780 A1 | 9/2016 | Hall et al. |
| 2016/0287251 A1 | 10/2016 | Shelton, IV et al. |
| 2016/0338764 A1 | 11/2016 | Krastins et al. |
| 2017/0010578 A1 | 1/2017 | Miyakawa |
| 2017/0042604 A1 | 2/2017 | McFarland et al. |
| 2017/0079710 A1 | 3/2017 | Deville et al. |
| 2017/0097035 A1 | 4/2017 | Zimmerman et al. |
| 2017/0135746 A1 | 5/2017 | Tetzlaff et al. |
| 2017/0189028 A1 | 7/2017 | Aranyi |
| 2017/0245857 A1 | 8/2017 | Shelton, IV et al. |
| 2017/0296172 A1 | 10/2017 | Harris et al. |
| 2018/0021042 A1* | 1/2018 | Nicholas .......... A61B 17/07207 606/207 |
| 2018/0161052 A1 | 6/2018 | Weir et al. |
| 2018/0168581 A1 | 6/2018 | Hunter et al. |
| 2018/0168622 A1 | 6/2018 | Shelton, IV et al. |
| 2018/0168628 A1* | 6/2018 | Hunter ................ A61B 34/30 |
| 2018/0168641 A1 | 6/2018 | Harris et al. |
| 2018/0168642 A1 | 6/2018 | Shelton, IV et al. |
| 2018/0168649 A1 | 6/2018 | Shelton, IV et al. |
| 2018/0310948 A1 | 11/2018 | Stamm et al. |
| 2019/0015124 A1 | 1/2019 | Williams et al. |
| 2019/0142531 A1 | 5/2019 | Wentworth et al. |
| 2019/0167266 A1 | 6/2019 | Patel et al. |
| 2019/0365458 A1 | 12/2019 | Whitlock et al. |
| 2020/0397430 A1 | 12/2020 | Patel et al. |
| 2021/0000557 A1 | 1/2021 | Mustufa et al. |
| 2021/0077101 A1 | 3/2021 | Patel et al. |
| 2021/0177495 A1 | 6/2021 | Ross et al. |
| 2021/0177500 A1 | 6/2021 | Khalaji |
| 2021/0212683 A1 | 7/2021 | Burbank |
| 2021/0386427 A1 | 12/2021 | Millman et al. |
| 2022/0015762 A1 | 1/2022 | Wixey et al. |
| 2022/0015763 A1 | 1/2022 | Wixey et al. |
| 2022/0015823 A1 | 1/2022 | Wilson et al. |
| 2022/0054130 A1 | 2/2022 | Overmyer et al. |
| 2022/0061836 A1 | 3/2022 | Parihar et al. |
| 2022/0061840 A1 | 3/2022 | Hites |
| 2022/0061841 A1 | 3/2022 | Wixey et al. |
| 2022/0071632 A1 | 3/2022 | Patel et al. |
| 2022/0079585 A1 | 3/2022 | Egan |

FOREIGN PATENT DOCUMENTS

| | | |
|---|---|---|
| EP | 1090592 A1 | 4/2001 |
| EP | 1728473 A1 | 12/2006 |
| EP | 1479346 B1 | 1/2007 |
| EP | 1621141 B1 | 7/2007 |
| EP | 1316290 B1 | 2/2012 |
| EP | 1754445 B1 | 10/2013 |
| EP | 3135225 A2 | 3/2017 |
| EP | 3173029 A1 | 5/2017 |
| FR | 2828952 B1 | 12/2005 |
| JP | 5301166 B2 | 9/2013 |
| JP | 2016508792 A | 3/2016 |
| JP | 2016513570 A | 5/2016 |
| JP | 2017527396 A | 9/2017 |
| JP | 6411461 B2 | 10/2018 |
| JP | 2019141659 A | 8/2019 |
| SU | 405234 A1 | 9/1975 |
| SU | 886900 A1 | 12/1981 |
| SU | 1333319 A2 | 8/1987 |
| SU | 1442191 A1 | 12/1988 |
| SU | 1459659 A1 | 2/1989 |
| WO | WO-8602254 A1 | 4/1986 |
| WO | WO-9005489 A1 | 5/1990 |
| WO | WO-9734533 A1 | 9/1997 |
| WO | WO-03094743 A1 | 11/2003 |
| WO | WO-03094746 A1 | 11/2003 |
| WO | WO-03094747 A1 | 11/2003 |

(56) References Cited

FOREIGN PATENT DOCUMENTS

| WO | WO-2012142872 A1 | 10/2012 |
|---|---|---|
| WO | WO-2014106275 A1 | 7/2014 |
| WO | WO-2017034803 A2 | 3/2017 |
| WO | WO-2017156070 A1 | 9/2017 |
| WO | WO-2017214243 A1 | 12/2017 |
| WO | WO-2018005750 A1 | 1/2018 |
| WO | WO-2018071497 A1 | 4/2018 |
| WO | WO-2018118402 A1 | 6/2018 |

OTHER PUBLICATIONS

International Preliminary Reporton Patentability for Application No. PCT/US2019/017646, dated Aug. 27, 2020, 10 pages.
International Preliminary Reporton Patentability for Application No. PCT/US2019/019501, dated Sep. 3, 2020, 7 pages.
International Search Report and Written Opinion for Application No. PCT/US2019/056979, dated Dec. 18, 2019, 8 pages.
International Search Report and Written Opinion for Application No. PCT/US2019/062344, dated Mar. 23, 2020, 17 pages.
International Search Report and Written Opinion for Application No. PCT/US2019/062768, dated Mar. 9, 2020, 15 pages.
International Search Report and Written Opinion for Application No. PCT/US2019/064861, dated Mar. 30, 2020, 18 pages.
International Search Report and Written Opinion for Application No. PCT/US2019/066513, dated Apr. 21, 2020, 8 pages.
International Search Report and Written Opinion for Application No. PCT/US2019/066530, dated Apr. 21, 2020, 8 pages.
International Search Report and Written Opinion for Application No. PCT/US2020/020672, dated Jun. 29, 2020, 10 pages.
International Search Report and Written Opinion for Application No. PCT/US2020/033481, dated Sep. 3, 2020, 22 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
United States Patent Office; International Search Report & Written Opinion; dated Apr. 16, 2019; PCT Application No. PCT/US2019/017646.
European Search Report (Corrected version) for Application No. EP19750317.0, dated Mar. 28, 2022, 26 pages.
International Search Report and Written Opinion for Application No. PCT/US2020/025655, dated Jul. 22, 2020, 8 pages.
International Search Report and Written Opinion for Application No. PCT/US2019/019501, dated May 9, 2019, 8 pages.
Partial European Search Report for Application No. EP19757451.0, dated Feb. 2, 2022, 12 pages.

\* cited by examiner

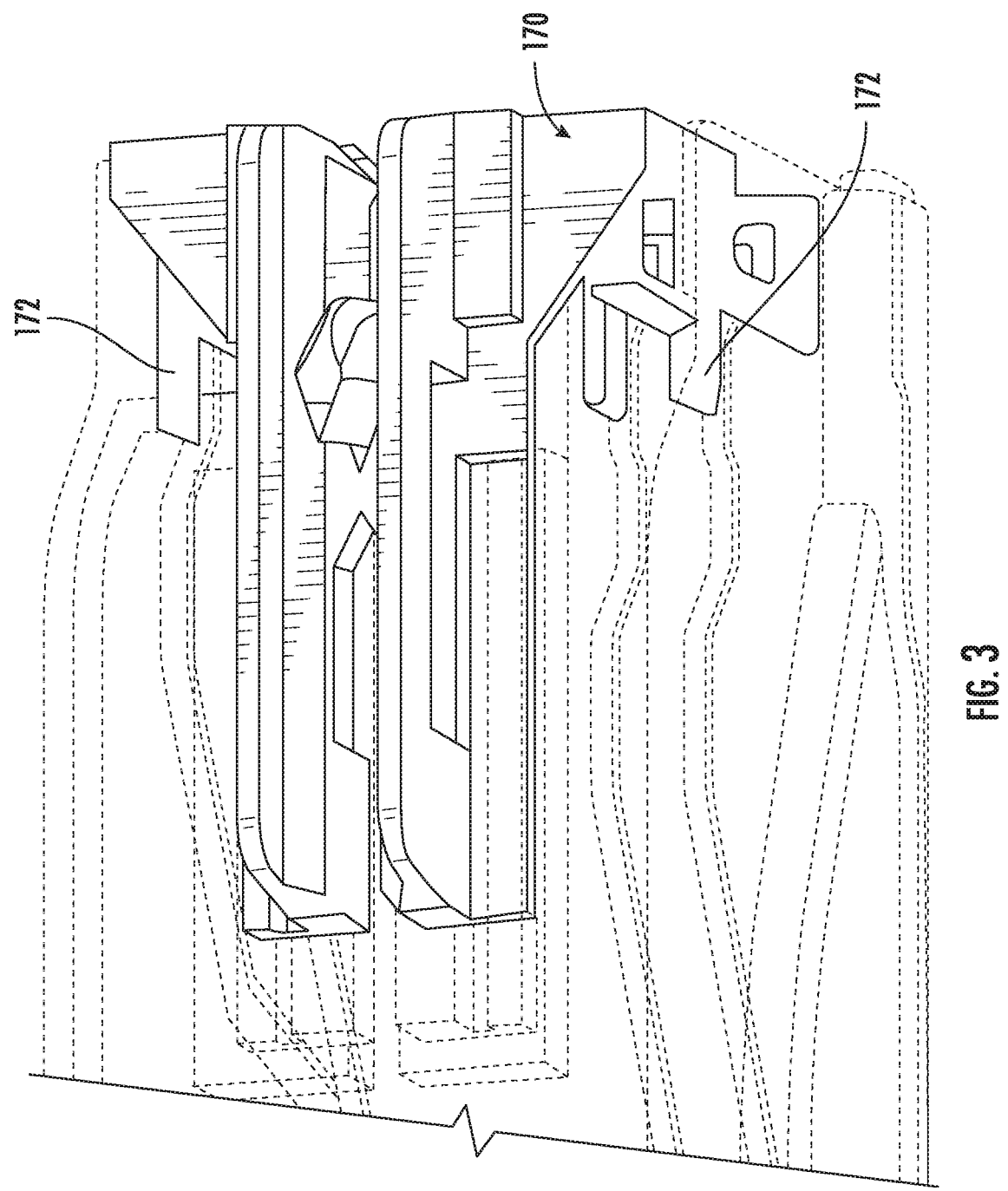

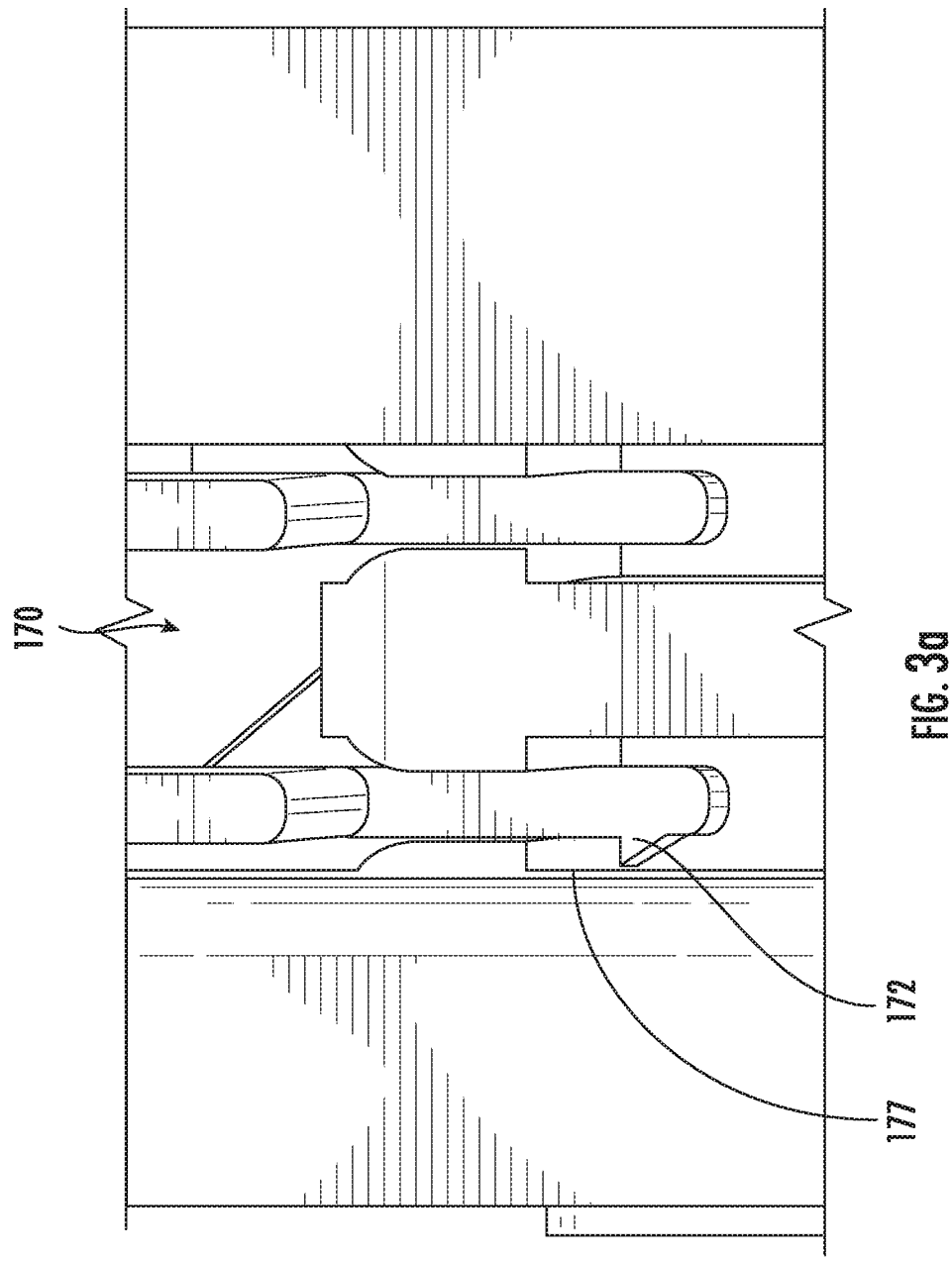

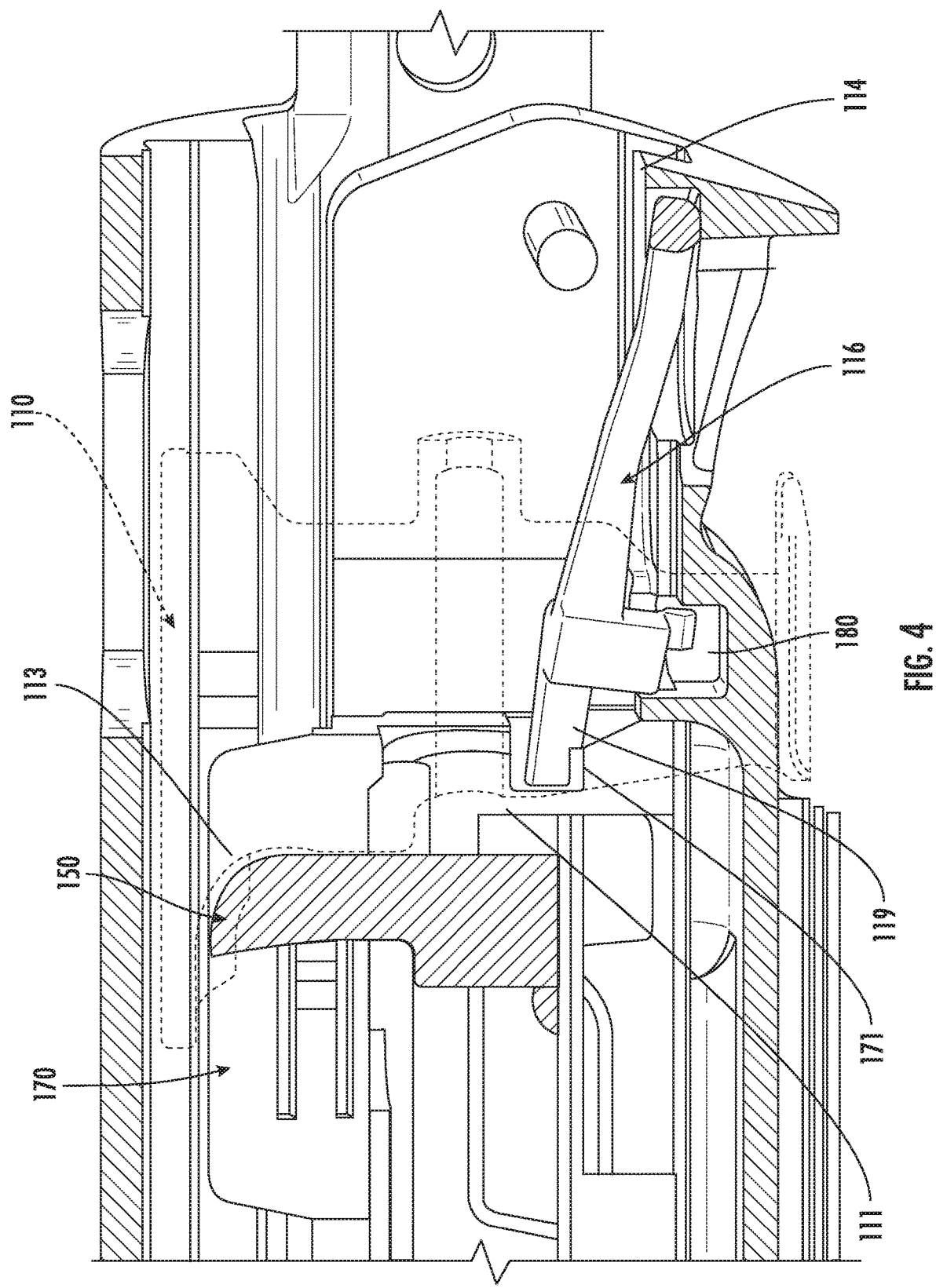

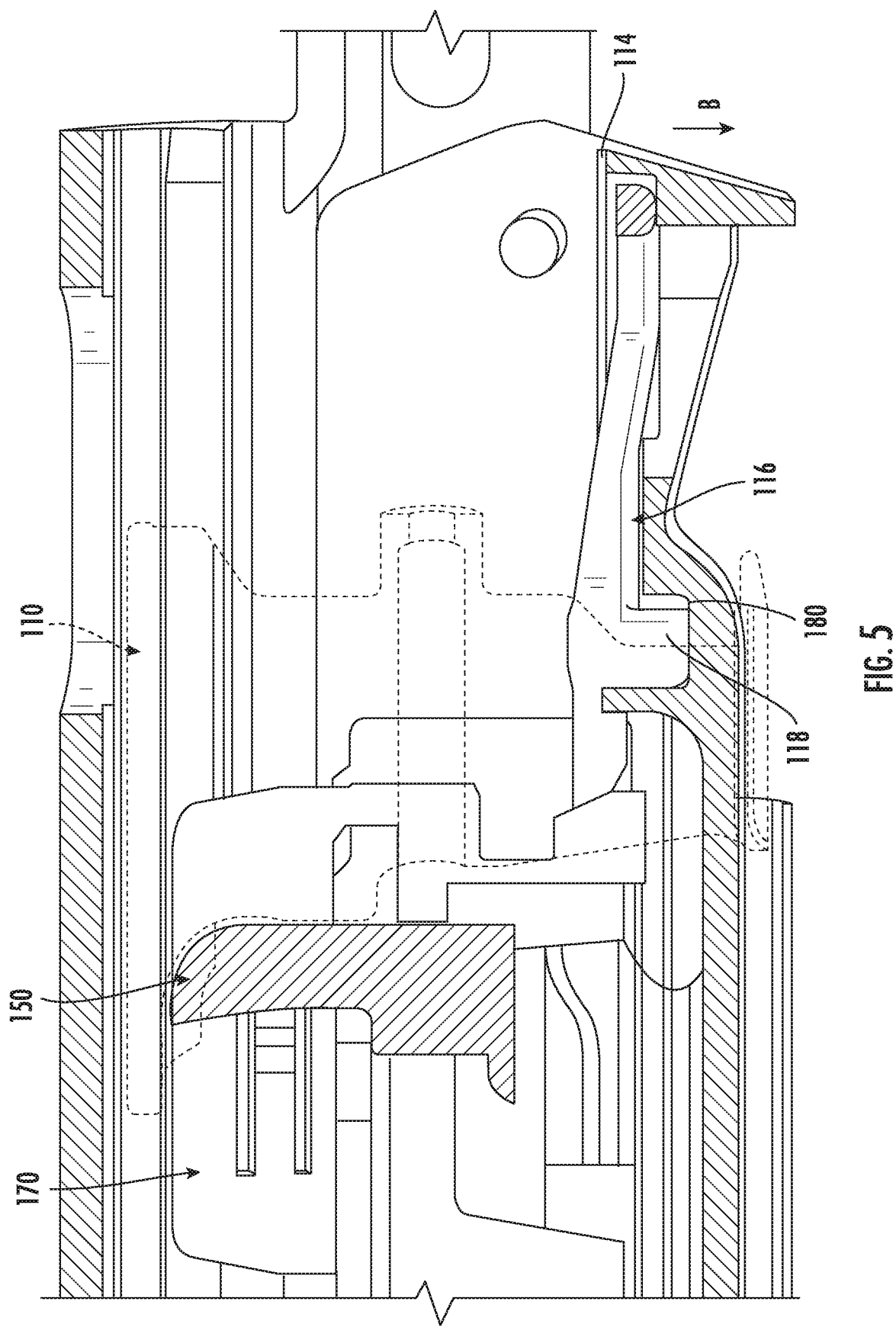

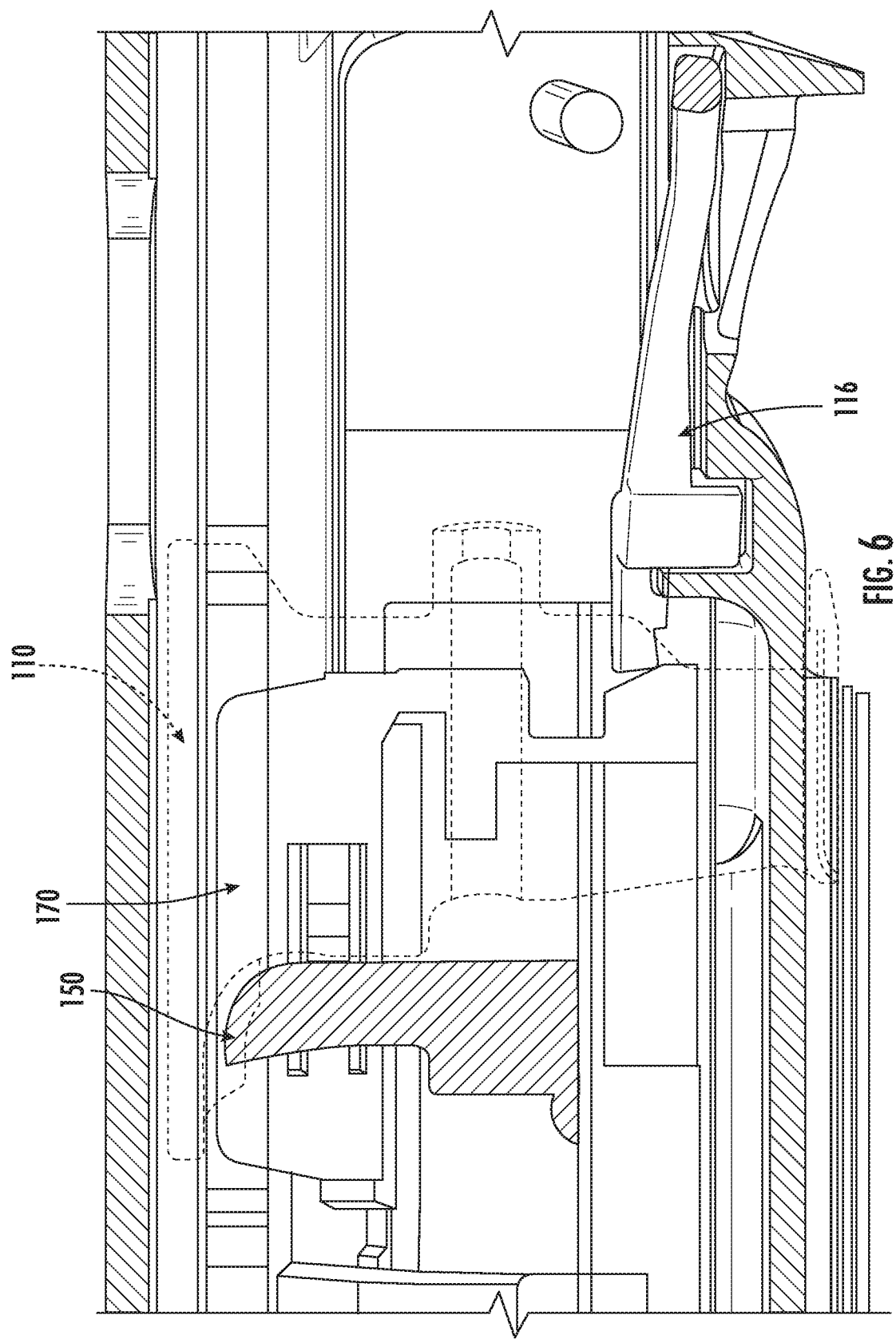

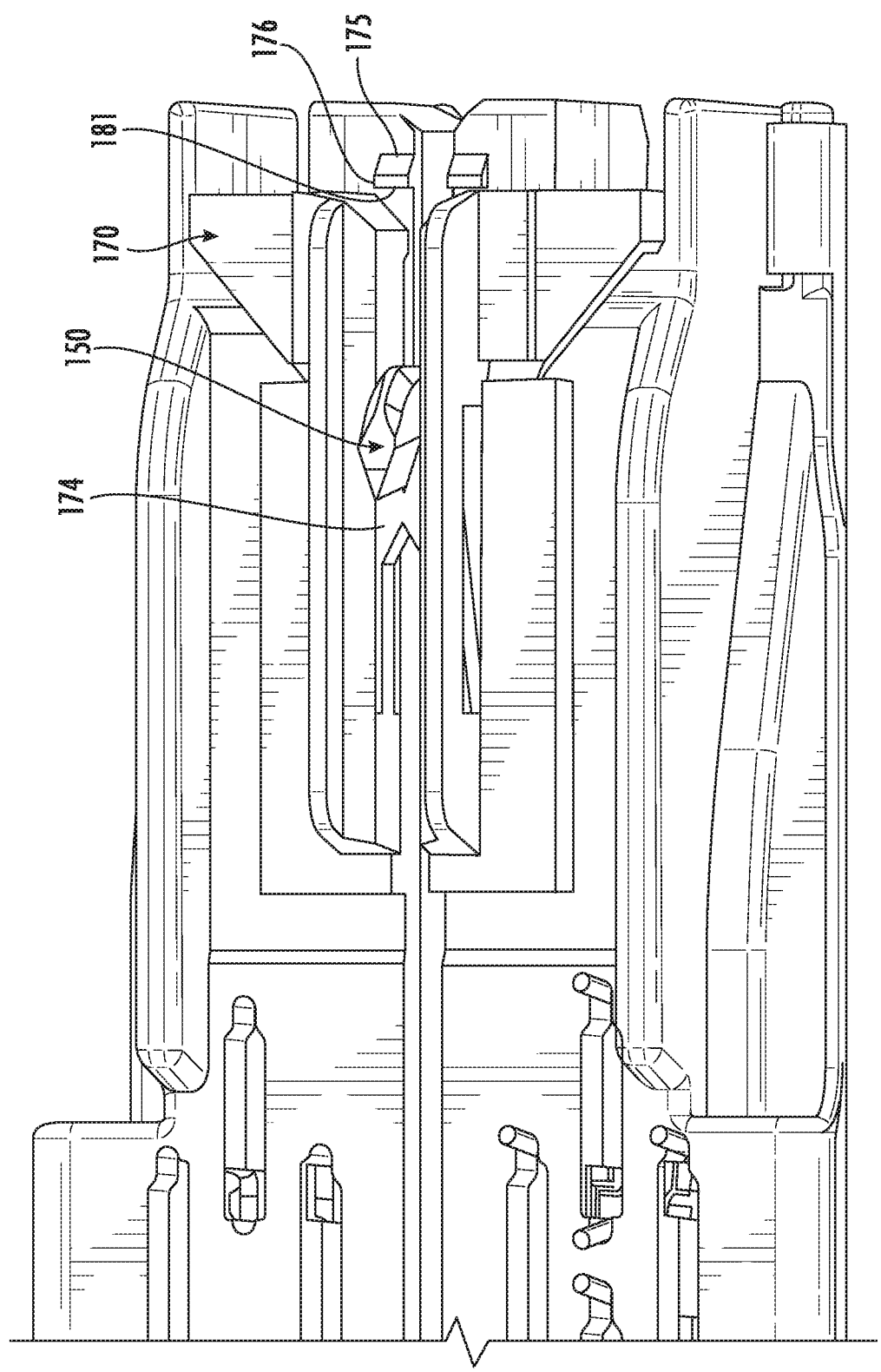

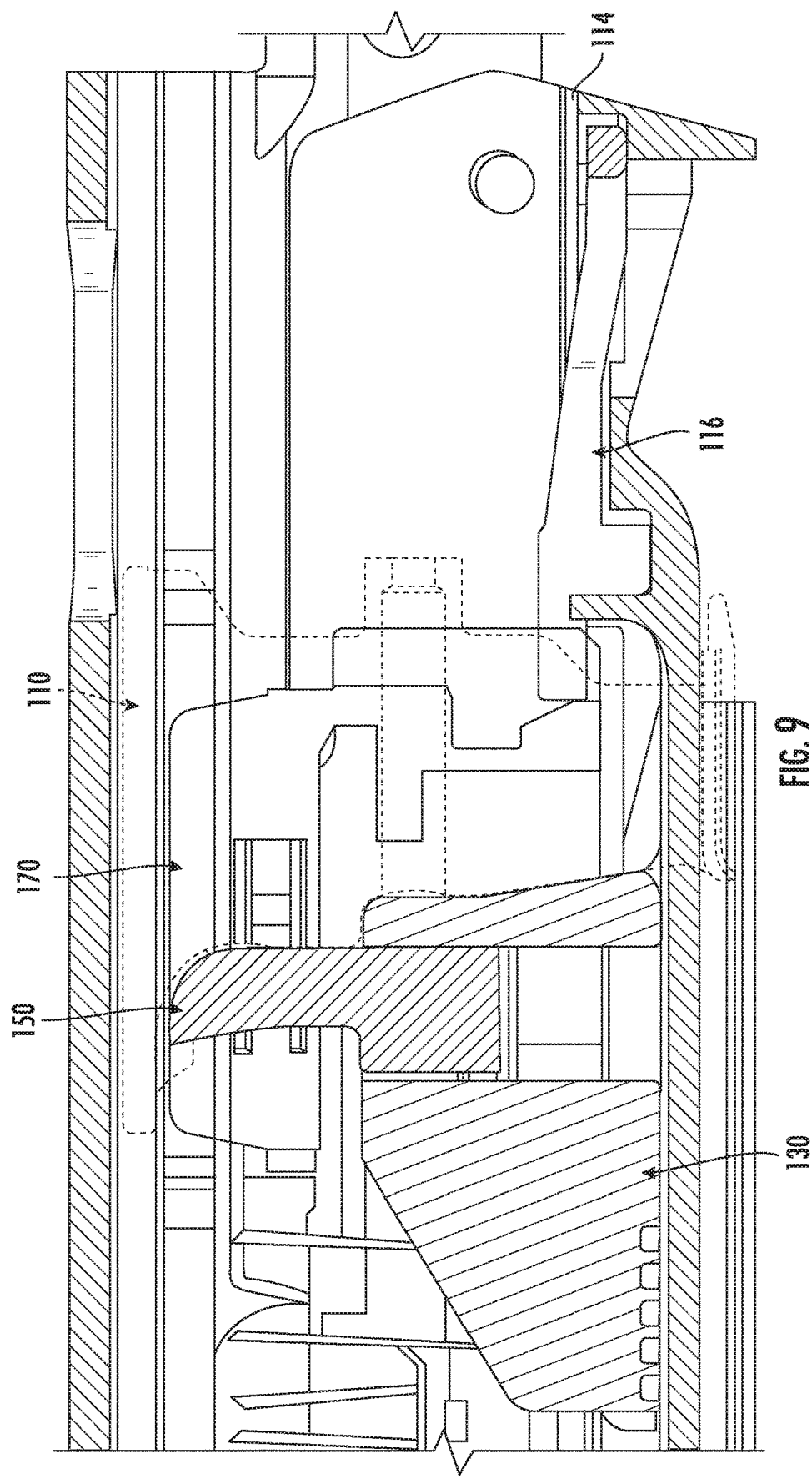

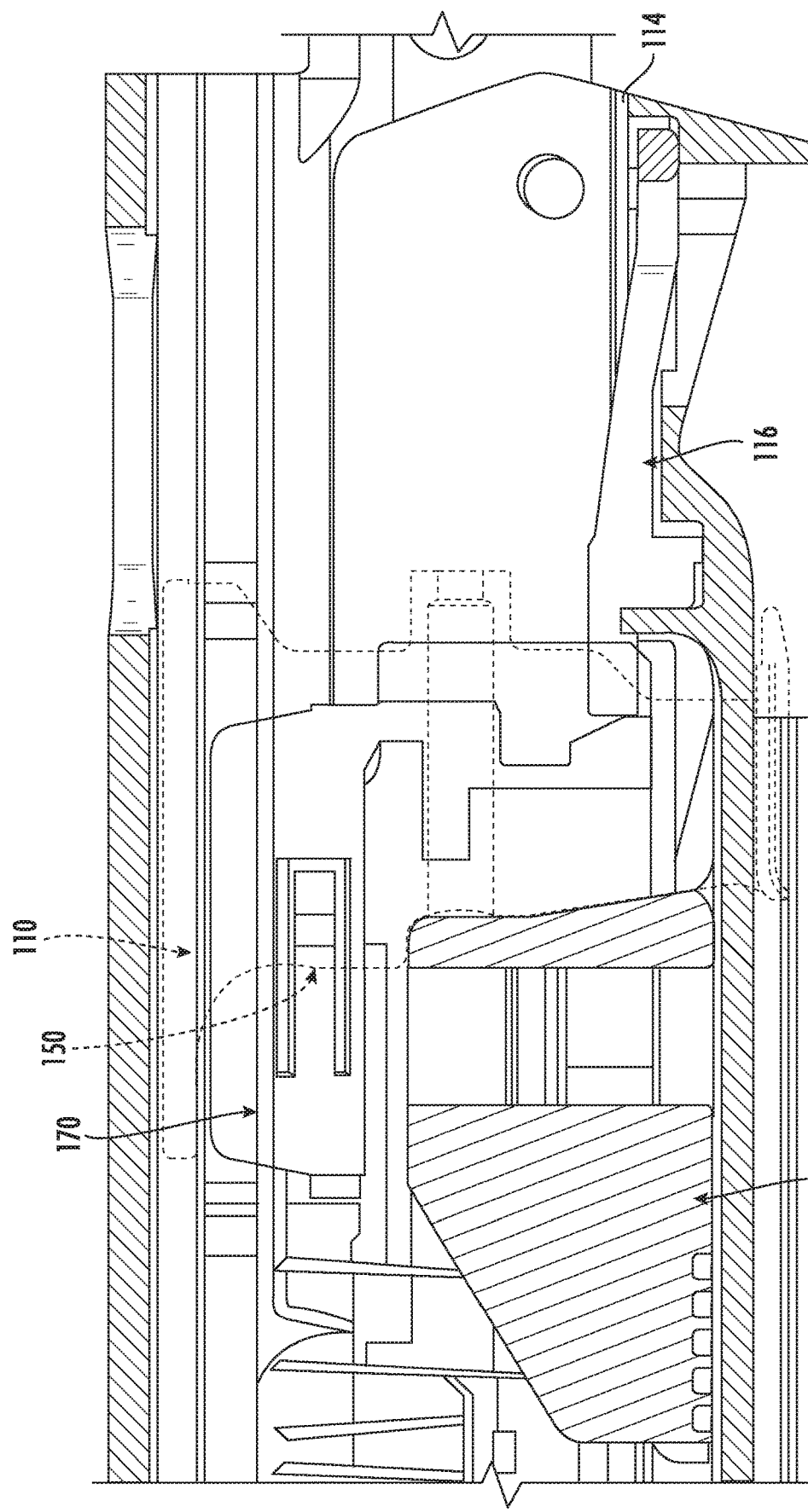

SURGICAL INSTRUMENT WITH LOCKOUT MECHANISM

CROSS REFERENCE TO RELATED APPLICATIONS

This application is the National Stage of International Application No. PCT/US19/17646 filed Feb. 12, 2019 which claims benefit of U.S. Provisional Application No. 62/629,572 filed Feb. 12, 2018, the entirety of which is herein incorporated by reference.

TECHNICAL FIELD

The present disclosure relates to surgical stapling instruments having a locking mechanism to prevent actuation of a knife when there is a spent or previously fired cartridge in place. More particularly, the present disclosure is directed towards locking assemblies for surgical clamping and cutting instruments include a locking member and a switch.

BACKGROUND

Surgical clamping and cutting instruments, such as, for example, surgical stapling instruments, may include an end effector having opposing jaws that clamp tissue and a knife that cuts the clamped tissue. It is often advantageous for an end effector of a surgical stapling instrument to be reusable. To that end, staple cartridges can be fitted into one jaw of the end effector prior to each use of the surgical stapling instrument.

It is desirable to prevent firing of a surgical stapling instrument while a spent cartridge remains in place on the jaw. Thus, a need exists for effective mechanisms to prevent firing of a surgical stapling instrument while a spent staple cartridge is in place in the end effector of the surgical stapling instrument.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure relates to surgical stapling instruments having a locking mechanism to prevent actuation of a knife when there is a spent or previously fired cartridge in place.

In one aspect, a lockout assembly for use with a surgical stapling instrument includes a locking member and a switch. A drive member is configured to releasably engage and translate at least one of a knife or a shuttle in a distal direction through a staple firing stroke. The locking member of the locking assembly is movable from a first position permitting distal translation of the drive member through the staple firing stroke, to a second position inhibiting distal translation of the drive member through the staple firing stroke. A spring may bias the locking member toward the second position. The switch of the locking assembly is movable from a proximal position to a distal position. When the switch is in the proximal position, the switch releasably maintains the locking member in the first position. When the switch is in the distal position, the switch disengages from the locking member thereby allowing the locking member to move to the second position.

In another aspect, a surgical stapling instrument includes an anvil jaw assembly, and a staple jaw assembly, including a knife and a shuttle. A drive member is configured to releasably engage and translate the knife and shuttle in a distal direction through a staple firing stroke. The knife and shuttle disengage from the drive member upon distal movement of the drive member after the staple firing stroke. The surgical stapling instrument further includes a locking member pivotable from a first position permitting distal translation of the drive member, to a second position preventing distal translation of the drive member. The surgical stapling instrument further includes a switch, that when in a proximal position, releasably maintains the locking member in the first position. When the switch is in a distal position, the switch disengages from the locking member thereby allowing the locking member to move to the second position.

In another aspect, a surgical stapling instrument includes an anvil jaw assembly, and a staple jaw assembly including a shuttle. The surgical stapling instrument further includes a drive member having a knife integrally formed on an edge thereof. The drive member is configured to releasably engage and translate the shuttle in a distal direction through a staple firing stroke. The shuttle disengages from the drive member upon subsequent distal movement of the drive member after the staple firing stroke. The surgical stapling instrument further includes a locking member pivotable from a first position permitting distal translation of the drive member, to a second position preventing distal translation of the drive member. The surgical stapling instrument further includes a switch, that when in a proximal position, releasably maintains the locking member in the first position. When the switch is in a distal position, the switch disengages from the locking member thereby allowing the locking member to move to the second position.

BRIEF DESCRIPTION OF THE DRAWINGS

The above and other aspects, features, and advantages of the present surgical stapling instruments having a locking mechanism will become more apparent in light of the following detailed description when taken in conjunction with the accompanying drawings in which:

FIG. 3 is a partial perspective view illustrating the end effector including a lockout assembly in accordance with the embodiment of FIG. 2 showing a proximally positioned switch of a surgical stapling instrument having an unfired reload is installed;

FIG. 3a is a partial perspective view illustrating the end effector including a lockout assembly in accordance with the embodiment of FIG. 2 illustrating a pair of retaining snaps of the switch engaging undercuts of the unfired reload;

FIG. 4 is a partial cross-sectional side view of the end effector including a lockout assembly in accordance with the embodiment of FIG. 2 with the drive member advanced to contact the knife;

FIG. 5 is a partial side, cross-sectional view of the end effector including a lockout assembly in accordance with the embodiment of FIG. 2 illustrating the switch advanced to a distal position;

FIG. 6 is a partial side, cross-sectional view of the end effector including a lockout assembly in accordance with the embodiment of FIG. 2 showing the knife cutting the switch;

FIG. 7 is a partial perspective view of the end effector including a lockout assembly in accordance with the embodiment of FIG. 2 showing an uncut switch that has been pushed to a distal position by the knife;

FIG. 9 is a partial cross-sectional side view of the end effector including a lockout assembly in accordance with the embodiment of FIG. 2 with the shuttle shown; and FIG. 10 is a partial cross-sectional side view of the end effector including a lockout assembly in accordance with the embodiment of FIG. 2 illustrating a drive member having an integrally formed knife on an edge thereof.

DETAILED DESCRIPTION

Particular embodiments of the present surgical stapling instruments are described hereinbelow with reference to the accompanying drawings; however, it is to be understood that the disclosed embodiments are merely exemplary of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in unnecessary detail.

The present disclosure relates to locking assemblies including a locking member and a switch. A drive member is configured to engage at least one of a knife or a shuttle of a surgical stapling instrument and to translate the knife and/or shuttle in a distal direction through a staple-firing stroke. Contact between the drive member and the knife and/or shuttle is releasable in that once the knife and/or shuttle are translated by the drive member in the distal direction through a staple firing stroke, the knife and/or shuttle disengage from the drive member, remain at a distal portion of the stapling instrument, and are not translated in a proximal direction by the drive member. The locking member is movable from a first position permitting distal translation of the drive member through the staple-firing stroke, and a second position inhibiting distal translation of the drive member through the staple-firing stroke. A spring is configured to bias the locking member toward the second position. The switch of the locking assembly is movable from a proximal position to a distal position. When the switch is in the proximal position, the switch releasably maintains the locking member in the first position. When the switch is in the distal position, the switch disengages from the locking member thereby allowing the locking member to move to the second position.

While the following disclosure is presented with respect to a linear surgical stapler where staples are sequentially fired, it should be understood that the present locking assemblies may be readily adapted for use in any type of surgical clamping and cutting instruments, whether or not the surgical clamping and cutting instrument applies a fastener. The surgical clamping and cutting instrument may be a minimally invasive (e.g., laparoscopic) instrument or an instrument used for open surgery.

Additionally, the present locking assemblies may be readily adapted for use in surgical instruments that are activated using any technique within the purview of those skilled in the art, such as, for example, manually activated surgical instruments, powered surgical instruments (e.g., electromechanically powered instruments), robotic surgical instruments, and the like.

Figure 1A:
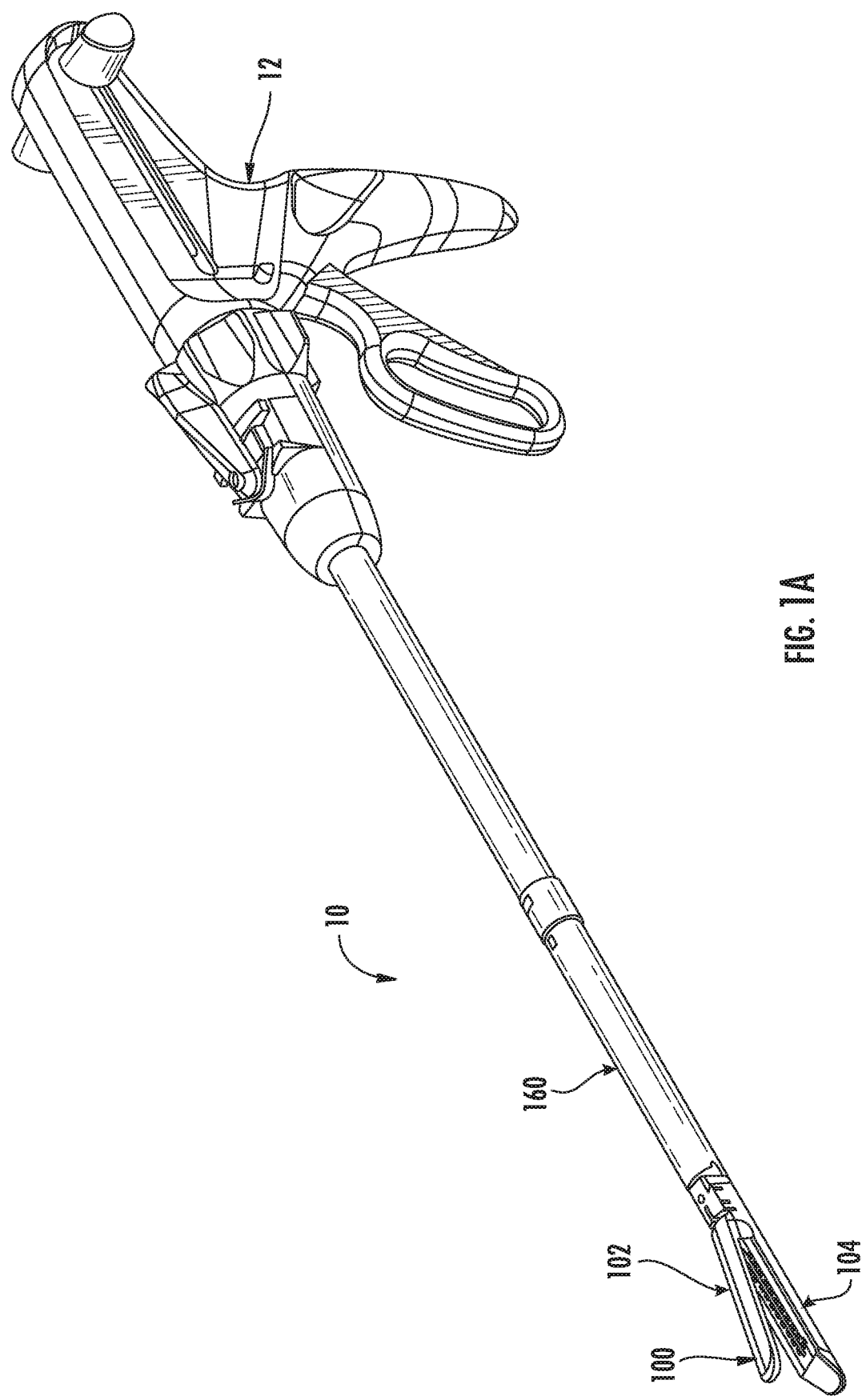
FIG. 1A is a perspective view of an illustrative surgical stapling instrument.

FIG. 1A is a perspective view of an illustrative surgical stapling instrument 10 capable of utilizing a locking assembly in accordance with the present disclosure. Surgical stapling instrument 10 includes a handle assembly 12, and an end effector 100 including an anvil jaw assembly 102 and a staple jaw assembly 104 mounted on an elongated shaft 160 of the surgical stapling instrument 10.

Figure 1B:
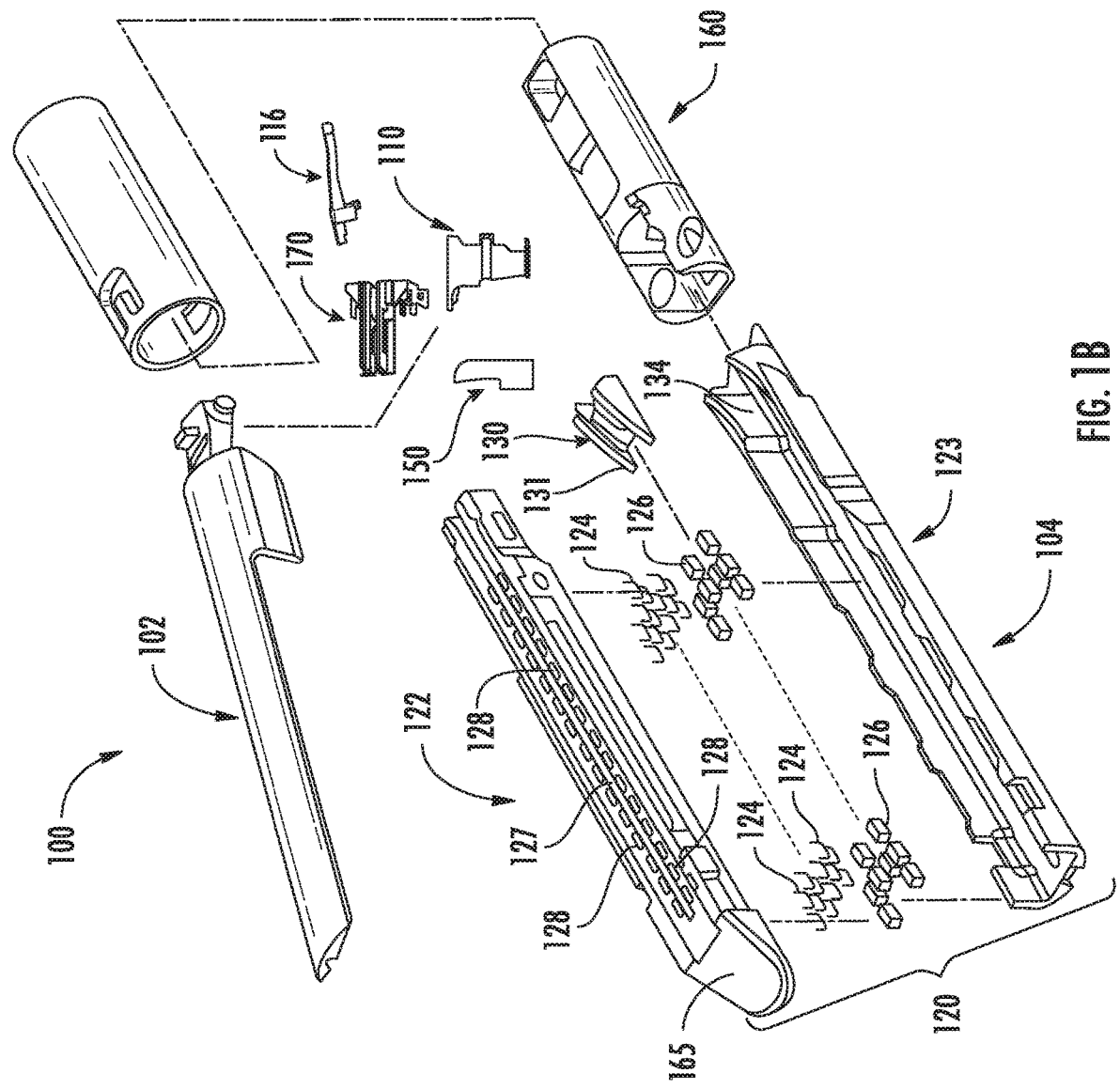
FIG. 1B is an exploded view of an illustrative end effector of a surgical stapling instrument.

FIG. 1B shows anvil jaw assembly 102, including an anvil 106 having staple forming pockets 103 (not shown) supported thereon, and staple jaw assembly 104. Staple jaw assembly 104 and anvil jaw assembly 102 are configured to move from an open position to a closed position. In the open position, a fresh stapling cartridge can be loaded into jaw assembly 104, a spent staple cartridge removed from jaw assembly 104, and tissue may be positioned between the jaw assemblies 102, 104. In the closed position, jaw assemblies 102, 104 cooperate to close upon and clamp tissue such that cartridge 122 and anvil 106 are in close cooperative alignment. In the embodiment shown in FIGS. 1A and 1B, staple jaw assembly 104 is stationary and anvil jaw assembly 102 pivots to the open position. In other embodiments it is contemplated that the jaw assembly containing the anvil is stationary and the jaw assembly containing the staple cartridge pivots to the open position. As those skilled in the art reading this disclosure will appreciate, in yet other embodiments both the anvil jaw assembly and the staple jaw assembly may pivot.

With continued reference to FIG. 1B, staple jaw assembly 104 includes a staple cartridge 122 supported in a channel 134 on a lower jaw 123. Cartridge 122 includes a plurality of staples 124 that are supported on corresponding staple drivers 126 provided within respective staple apertures 128 formed in cartridge 122. Cartridge 122 also includes a shuttle 130 having an inclined distal portion 131 that, upon distal movement, sequentially acts on staple drivers 126, camming them upwardly thereby moving staples 124 into deforming contact with anvil 106. Cartridge 122 also includes a knife 150 configured to translate distally through a channel 127 in cartridge 122 and sever clamped, stapled tissue.

FIG. 1B further shows a drive member 110 that is movably supported on the surgical stapling instrument such that it may pass distally through cartridge 122 and staple jaw assembly 104 when the surgical stapling instrument is fired (e.g., actuated). Also shown in FIG. 1B is the locking assembly including locking member 116 on staple jaw assembly 104 and switch 170 on cartridge 122.

For a more detailed description of illustrative end effectors, reference may be made to U.S. Pat. Nos. 6,669,073 and 8,800,841, the entire contents of which are incorporated herein by this reference. It should of course, be understood that end effector shown in FIGS. 1A and 1B is merely illustrative, and that other end effectors may be employed, including but not limited to the end effectors shown in WO2014/106275, the entire contents of which are incorporated herein by this reference.

Figure 2:
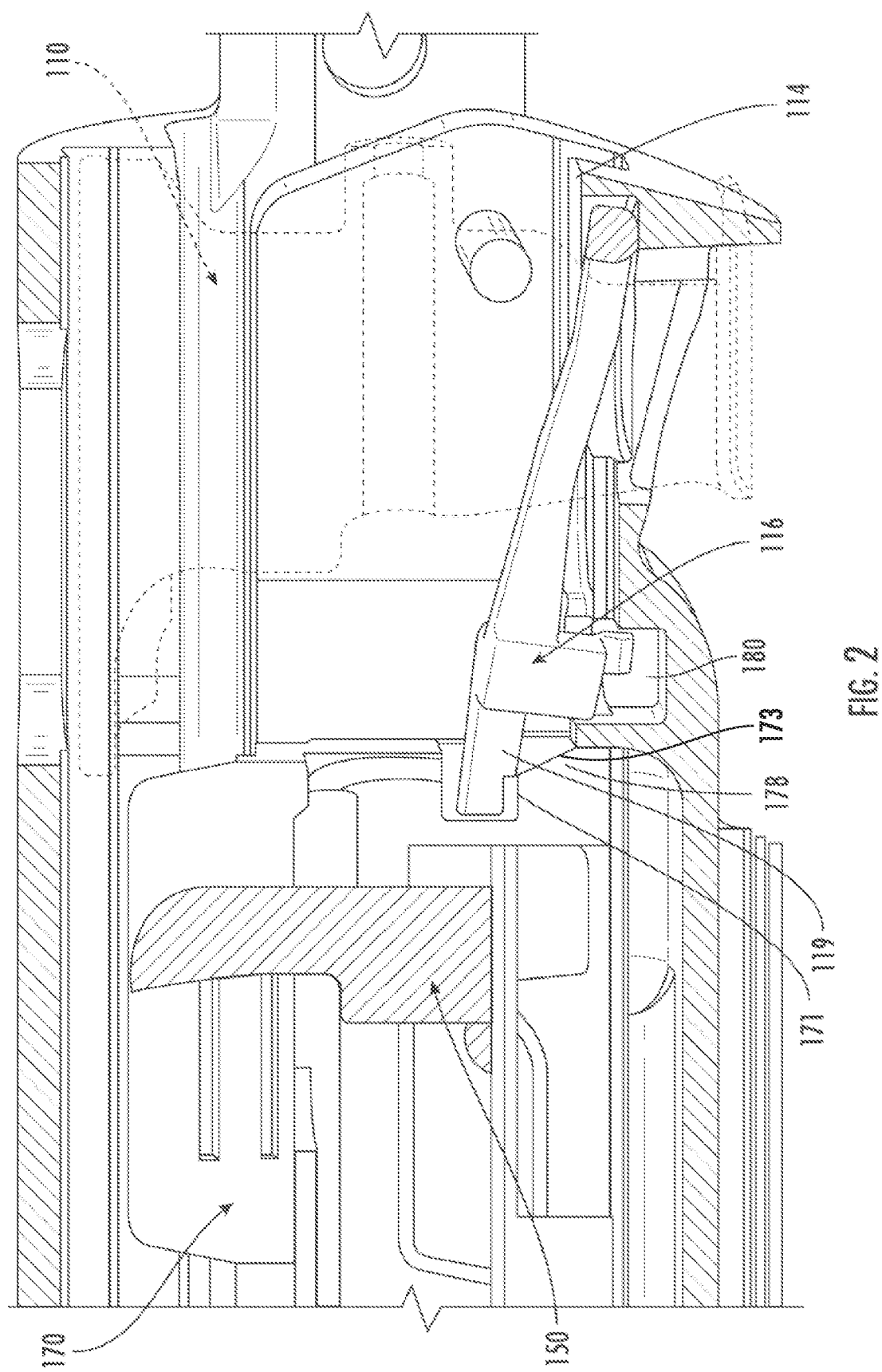
FIG. 2 depicts a partial cross-sectional side view of the end effector of a surgical stapling instrument including a lockout assembly in accordance with an embodiment of the present disclosure having an unfired reload installed.

FIG. 2 shows an illustrative surgical stapling instrument with an unfired reload installed, including drive member 110, spring 114, locking member 116, knife 150, switch 170, and slot 180.

In a fresh reload, drive member 110 is in a proximal position where it has not yet engaged knife 150. Drive member 110 may be any structure capable of pushing at least one of a shuttle or a knife of a surgical stapling instrument with the necessary force to effectively sever or staple human tissue. Drive member 110 may be an I-beam, an E-beam, or any other type of drive member capable of performing similar functions. Drive member 110 includes a lower distal portion 111 and upper distal portion 113.

When an unfired reload is installed, as in FIG. 2, switch 170 is in a first proximal position. In a fresh, unfired reload distal portion 119 of locking member 116 rests on shelf 171 of switch 170, keeping engagement portion 118 of locking member 116 above and out of engagement with slot 180. When locking member 116 is in this disabled position, distal translation of drive member 110 is permitted, as locking member 116 will not obstruct movement of drive member 110.

As seen in FIG. 3, an unfired reload containing a new cartridge, knife 150 is located on the proximal side of central portion 174 of switch 170, which is uncut. Upon installation of an unfired reload, as depicted in FIG. 3a, retaining snaps 172 of switch 170 are configured to engage undercuts 177 formed on the unfired reload. This interaction, which may be a snap-fit interaction, retains the switch in the proximal position prior to firing of the surgical stapling instrument.

Upon initiation of the staple-firing stroke, as seen in FIG. 4 drive member 110 moves distally to contact knife 150. At this point in the actuation stoke, locking member 116 remains out of engagement with slot 180 because distal portion 119 of the locking member continues to rest on shelf 171 of switch 170. In this position, upper distal portion 113 of drive member 110 contacts knife 150 for distal translation as the actuation stroke continues. Lower distal portion 111 of drive member 110 similarly moves distally in order to engage and translate shuttle 130 (see FIG. 9).

As illustrated in FIG. 5, as drive member 110 continues to move distally, knife 150 begins to advance. Knife 150 is in contact with, and therefore pushes and translates, switch 170 from a proximal position, to a distal position. As illustrated in FIG. 5, once in the distal position, switch 170 separates from and no longer supports distal portion 119 of locking member 116 which essentially falls off of shelf 171. As a result, engagement portion 118 of locking member 116 falls into and engages slot 180, enabling the lockout. Spring 114 is configured to bias engagement portion 118 of locking member 116 in the direction of Arrow "B", urging engagement portion 118 to drop into slot 180 to enable the locking mechanism.

Figure 6A:
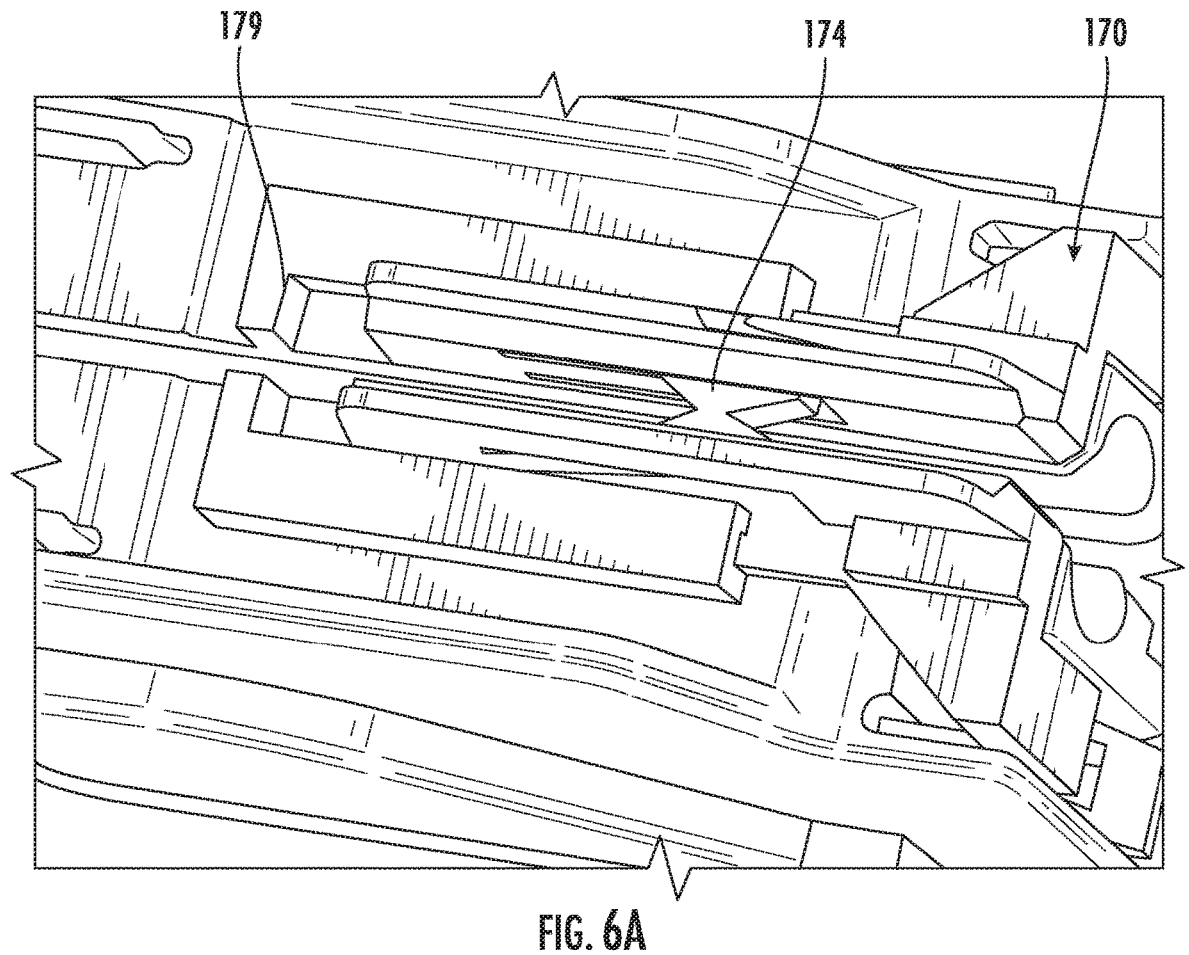
FIG. 6a is a partial perspective view of the end effector including a lockout assembly in accordance with the embodiment of FIG. 2 showing a distal wall blocking the switch from translating distally.

In FIG. 6, switch 170 is in the distal position. Once switch 170 is translated distally, further distal translation is prevented as switch 170 becomes obstructed by distal wall 179 as best seen in FIG. 6a. As a result of this obstruction, continued distal translation of knife 150 cuts through central portion 174 of switch 170 (see FIG. 7), as a result of the force provided by drive member 110 translating knife 150 distally. A perspective view of switch 170 in the second distal position is shown in FIG. 7 just before cutting of central portion 174. FIG. 7 also illustrates stops 176, each including a proximal ramped face 175. As drive member 110 translates knife 150 distally, and knife 150 pushes switch 170 distally, switch 170 rides over ramped faces 175 of stops 176. Distal faces 181 of stops 176 prohibit movement of switch 170 back to its initial proximal position.

Figure 8:
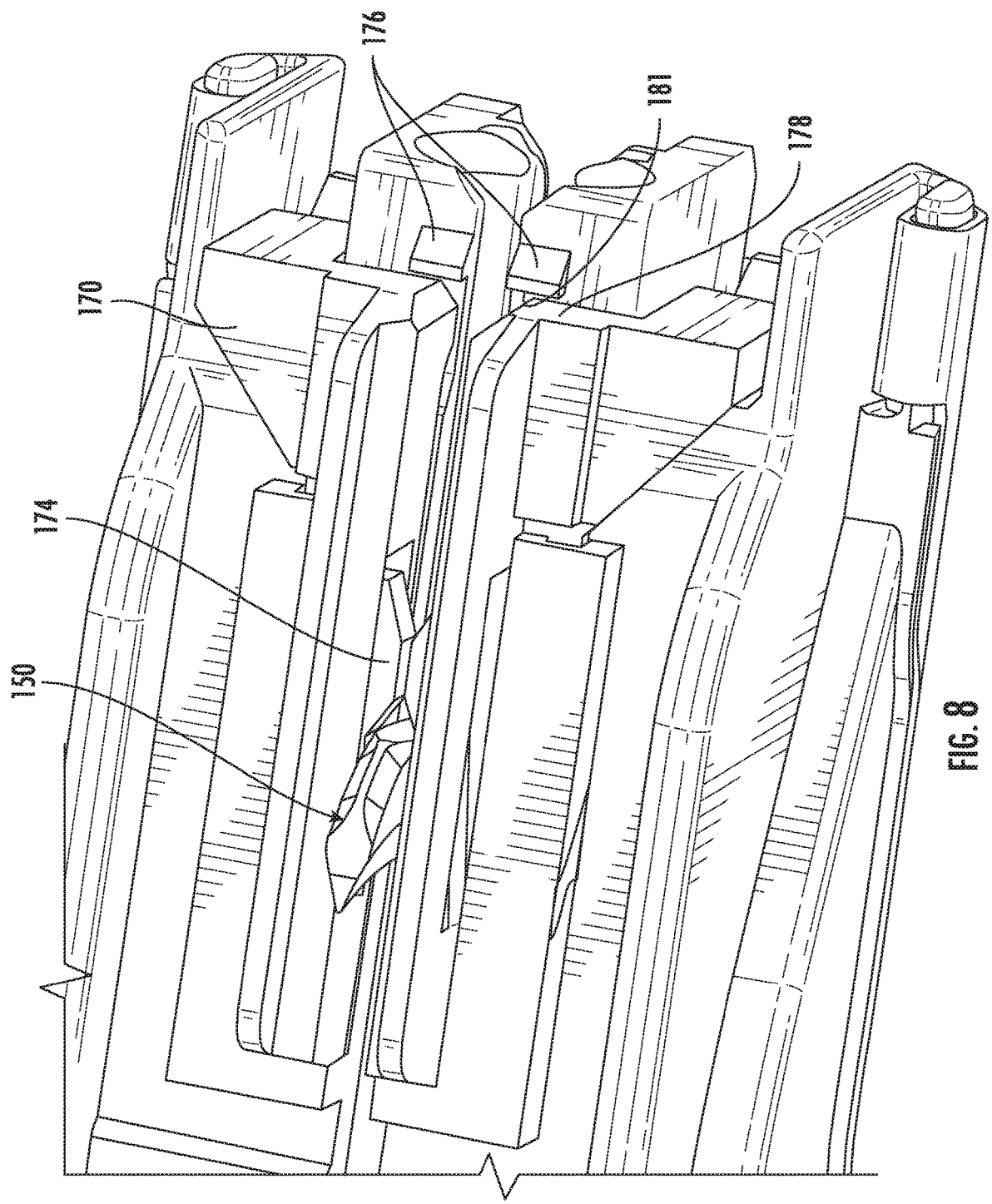
FIG. 8 is a partial perspective view of the end effector including a lockout assembly in accordance with the embodiment of FIG. 2 having a cut switch that is prevented from retracting by a pair of stops.

In FIG. 8, knife 150 has cut through central portion 174 of switch 170 so that knife 150 may continue to translate distally towards a final, parked position. As illustrated, stops 176 are positioned on the proximal side of switch 170. In this position, retraction of switch 170 is impossible, as the proximal portions 178 of switch 170 abut distal faces 181 of stops 176. By preventing switch 170 from retracting, it is ensured that locking member 116 may not be disengaged, while also keeping both cut parts of switch 170 contained in the reload.

Once drive member 110 translates distally through a complete firing stroke during which stapling and severing of tissue have occurred, drive member 110 can be retracted, leaving knife 150 parked at a position in a distal portion of cartridge 122. In embodiments, such as the embodiment illustrated in FIG. 9 a shuttle 130 may be unable to move proximally towards the home position due to friction with cartridge 122. In embodiments, as illustrated in FIG. 10, knife 150 may be integrally formed with drive member 110. In embodiments, knife 150 may be parked in a predetermined position in a distally located garage 165. The garage 165 including lateral surfaces that face the cutting tip of knife 150. As drive member 110 is retracted, engagement portion 118 of locking member 116 is unable to move upwards out of slot 180, as spring 114 retains it in the locked position.

Further retraction of drive member 110 positions locking member 116 distal of the drive member. Because the staple cartridge is spent and there is no proximally positioned switch to hold the locking member out of engagement with slot 180, any attempt to re-fire the surgical stapling instrument will be prevented by drive member 110 engaging locking member 116.

In order to disable the lockout of the surgical stapling instrument, an unfired reload (i.e. a new cartridge) must be installed. Each new cartridge contains a new switch 170, shuttle 130, and knife 150. When a new cartridge is installed, switch 170 moves proximally causing a distal portion 119 of locking member 116 to engage with and ride upwards along proximal ramped surface 173 of switch 170, until locking member 116 is again resting on shelf 171, as may be seen in FIG. 2. The lockout is then disabled, allowing for a user to again fire the surgical stapling instrument.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

What is claimed is:

1. A surgical stapling instrument comprising:
   first and second jaws;
   a drive member configured to move in a distal direction through one of the jaws; and
   a locking assembly including a locking member pivotable between a first position permitting distal translation of the drive member, and a second position preventing distal translation of the drive member;
   a switch movable from a proximal position to a distal position, wherein when the switch is in the proximal position the switch releasably maintains the locking member in the first position, and wherein when the switch is in the distal position the switch disengages from the locking member thereby allowing the locking member to move to the second position; and
   wherein the locking member engages a slot in one of the first and second jaws when in the second position, wherein the drive member is configured to pass through a portion of the switch as the drive member is moved in the distal direction through one of the jaws.

2. The surgical stapling instrument of claim 1, wherein one of the first and second jaws comprises a removable staple cartridge containing a knife and wherein the drive member is configured to releasably engage and translate the knife in the distal direction.

3. The surgical stapling instrument of claim 2, wherein the knife is configured to cut through a center portion of the switch.

4. The surgical stapling instrument of claim 1, wherein one of the first and second jaws comprises a shuttle and wherein the drive member is configured to releasably engage and translate the shuttle in the distal direction.

5. The surgical stapling instrument of claim 1, wherein one of the first and second jaws comprises a removable staple cartridge containing the switch.

6. The lockout assembly of claim 5, wherein one of the first and second jaws includes a channel configured to receive the staple cartridge.

7. The surgical stapling instrument of claim 1, further comprising a spring configured to bias the locking member towards the second position.

8. The surgical stapling instrument of claim 1, wherein the switch is prevented from moving proximally after the switch has been moved to the distal position.

9. The surgical stapling instrument of claim 1, wherein one of the first and second jaws further includes a pair of stops configured to prevent movement of the switch to the proximal position after the switch has been moved to the distal position.

10. The surgical stapling instrument of claim 1, wherein the drive member is actuated by a control device of a robotic surgical system.

\* \* \* \* \*